US006037150A

United States Patent [19]

Iatrou et al.

[11] Patent Number: 6,037,150
[45] Date of Patent: Mar. 14, 2000

[54] INSECT SEQUENCES FOR IMPROVING THE EFFICIENCY OF SECRETION OF NON-SECRETED PROTEINS IN EUKARYOTIC CELLS

[75] Inventors: Kostas Iatrou; Patrick J. Farrell; Leo A. Behie, all of Calgary, Canada

[73] Assignee: University Technologies International Inc., Calgary, Canada

[21] Appl. No.: 09/136,421

[22] Filed: Aug. 20, 1998

Related U.S. Application Data

[60] Provisional application No. 60/056,871, Aug. 21, 1997.

[51] Int. Cl.$^7$ .......................... C12P 21/02; C12N 15/85; C12N 5/10; C12N 9/16; C07H 21/04

[52] U.S. Cl. ................. 435/69.7; 435/69.1; 435/69.8; 435/320.1; 435/196; 435/325; 435/348; 435/455; 435/456; 435/471; 435/475; 536/23.4; 536/23.5; 536/23.51; 536/23.72; 536/24.1; 536/24.2

[58] Field of Search ............................... 435/69.1, 320.1, 435/325, 348, 455, 456, 471, 475; 536/23.1, 23.4, 23.5, 23.51, 23.72, 24.1, 24.2

[56] References Cited

U.S. PATENT DOCUMENTS

| | | | |
|---|---|---|---|
| 5,155,037 | 10/1992 | Summers | 435/348 |
| 5,516,657 | 5/1996 | Murphy et al. | 435/69.3 |
| 5,541,087 | 7/1996 | Lo et al. | 435/69.7 |
| 5,547,871 | 8/1996 | Black et al. | 435/348 |
| 5,565,362 | 10/1996 | Rosen | 435/320.1 |
| 5,571,720 | 11/1996 | Grandics et al. | 435/286.1 |
| 5,576,195 | 11/1996 | Robinson et al. | 435/69.8 |
| 5,726,044 | 3/1998 | Ming et al. | 435/69.7 |

FOREIGN PATENT DOCUMENTS

| | | |
|---|---|---|
| 0 608 696 | 8/1994 | European Pat. Off. . |
| WO94/03588 | 2/1994 | WIPO . |
| WO95/17515 | 6/1995 | WIPO . |

OTHER PUBLICATIONS

Lo et al., (1998) "High level expression and secretion of Fc–X fusion proteins in mammalian cells", *Protein Engineering* 11(6):495–500.

Bonning, et al., (1994) "Superior expression of juvenile hormone esterase and β–galactosidase from the base protein promoter of *Autographica californica* nuclear polyhedrosis virus compared to the p10 protein and polyhedrin promoters" *Journal of General Virology* 75:1551–1556.

Bonning and Hammock, (1996) "Development of Recombinant Baculoviruses for Insect Control" *Annual Review of Entomology* 41:191–210.

Brinster et al., (1988) "Introns increase transcriptional efficiency in transgenic mice" *PNAS* U.S.A. 85:836–840.

Chai, et al., (1993) "Glycosylation and high–level secretion of human tumour necrosis factor–β in recombinant baculovirus–infected insect cells" *Biotechnol. Appl.. Biochem* 18:259–273.

Clément and Jehanno, (1995) "Secretion of a bacterial protein by mammalian cells" *Journal of Biotechnology* 43:169–181.

Collins, et al. (1994) "Cloning and expression of bovine and porcine interleukin–2 baculovirus and analysis of species cross–reactivity" *Veterinary Immunology and Immunopathology* 40:313–324.

Congote and Li, (1994) "Accurate processing and secretion in the baculovirus expression system of an erythroid–cell––stimulating factor consisting of a chimaera of insulin–like growth factor II and an insect insulin–like peptide" *Biochem J.* 299:101–107.

Cottrez, et al., (1994) "Murine interleukin–4 production with a baculovirus:an easy and rapid method for a small scale production of functional interleukins" *Eur. Cytokine Netw.* 5(5):481–487.

Davis and Wood (1995) "Intrinsic glycosylation potentials of insect cell cultures and insect larvae" in vitro *Cell. Dev. Biol.* 31:659–663.

Garnier et al., (1994) "Scale–up of the adenovirus expression system for the production of recombinant protein in human 293S cells" *Cryotechnology* 15(1–3):145–155.

Hanzlik et al., (1989) "Isolation and Sequencing of a cDNA clones coding for juvenile hormone esterase from *Heliothis virescens*" *J. Biol. Chem.*264(21):12419–12425.

Huybrechts et al. (1992) "Nucleotide sequence of a trans-activating *Bombyx mori* nuclear polyhedrosis virus immediate early gene" *Biochim. Bioph. Acta.* 1129:328–330.

Jarvis and Summers, (1989) "Glycosylation and secretion of human tissue plasminogen activator in recombinant baculovirus–infected cells." *Mol Cell Biology* 9:214–223.

Johnson et al., (1992) "A cellular promoter–based expression cassette for generating recombinant baculoviruses directing rapid expression of passenger genes in infected insects" *Virology* 190:815–823.

Keil (1971) "Trypsin" in *The Enzymes*, Academic Press, 3:249–275.

Kroll et al., (1993) "A multifunctional prokaryotic protein expression system: Overproduction, affinity Purification and Selective Detection" *DNA and Cell Biology* 12:441–453.

Kunkel (1985) "Rapid and efficient site–specific mutagenesis without phenotypic selection" *Proc. Nat. Acad. Sci. U.S.A.* 82:488–492.

Lu et al., (1996)"Trans–activation of a cell housekeeping gene promoter by the IE1 gene product of baculoviruses" *Virology* 218:103–113.

Maiorella et al. (1988) "Large scale insect culture media for recombinant protein production" *Bio/Technology* 6:1406–1410.

(List continued on next page.)

Primary Examiner—David Guzo
Attorney, Agent, or Firm—Burns, Doane, Swecker & Mathis, L.L.P.

[57] ABSTRACT

An expression cassette useful for the secretion of a heterologous protein from eukaryotic cells comprising a DNA sequence encoding a promoter functionally linked to a DNA sequence coding for the juvenile hormone esterase gene which is linked in frame to a heterologous gene is disclosed. Also disclosed is a method of secreting heterologous proteins in eukaryotic cells.

17 Claims, 5 Drawing Sheets

OTHER PUBLICATIONS

Martens et al., (1995) "Characterization of baculovirus insecticides expressing tailored *Bacillus thuringiensis* Cry-lA(b) crystal proteins" *J. of Invertebrate Pathology* 66:249–257.

Martin–Eauclaire, et al., (1994) "Production of active, insect–specific scorpion neurotoxin in yeast" *Eur. J., Biochem.* 223:637–645.

Mounier and Prudhomme, (1986) "Isolation of actin genes in *Bombyx mori*: the coding sequence of a cytoplasmic actin gene expressed in the silk gland is interrupted by a single intron in an unusual position" *Biochimie* 68:1053–1061.

Mroczkowski, et al., (1994) "Secretion of thermostable DNA polymerase using a novel baculovirus vector" *The Journal of Biological Chemistry* 269(18):13522–13528.

O'Reilly et al., (1992) *Baculovirus Expression Vectors.* W.H. Freeman and Co.

Sareneva, et al. (1994) "Role of N–glycosylation in the synthesis, dimerization and secretion of human interferon–$\gamma$" *Biochem J.* 303:831–840.

Tzertziniz et al, (1994) "BmCF1, a *Bombyx mori* RXR–type receptor related to the *Drosophila ultraspiracle*", *Journal of Molecular Biology* 238:479–486.

Wu, et al., (1994) "Heterologous protein expression affects the death kinetics of baculovirus–infected insect cell cultures: a quantitative study by use of $\eta$–target theory" *Biotechnol. Prog.* 10:55–59.

Yamashina, (1956) "The action of enterokinase on trypsinogen" *Preliminary Notes* 20:433–434.

```
  19        A TGACTTCACA CGTACTCGCG CTCGCCTTCC
  51 TTCTACACGC GTGCACAGCG CTGGCGTGGC AGGAGACAAA TTCGCGCAGC
 101 GTGGTCGCCC ATCTGGACTC CGGCATTATA CGCGGCGTGC CGCGCTCAGC
 151 GGATGGCATC AAGTTCGCCA GCTTCCTAGG AGTGCCCTAC GCTAAGCAGC
 201 CTGTTGGAGA ACTCAGGTTT AAGGAGCTCG AGCCTCTAGA ACCTTGGGAT
 251 AATATCCTGA ACGCAACAAA TGAAGGACCC ATCTGCTTCC AAACAGATGT
 301 ATTATACGGG AGGCTCATGG CGGCAAGCGA GATGAGCGAG GCTTGCATAT
 351 ACGCCAACAT TCATGTTCCA TGGCAAAGCC TTCCCCGAGT GAGGGGGACC
 401 ACACCTTTAC GGCCTATCCT GGTGTTCATA CATGGTGGAG GATTTGCTTT
 451 CGGCTCCGGC CACGAGGACC TACACGGACC AGAATATTTG GTCACTAAGA
 501 ATGTCATCGT CATCACGTTT AATTACAGAT TGAACGTCTT CGGTTTCCTG
 551 TCCATGAACA CAACAAAAAT CCCCGGGAAT GCCGGTCTCC GGGATCAGGT
 601 AACCCTGTTG CGCTGGGTGC AAAGGAACGC CAAGAATTTC GGAGGAGACC
 651 CCAGCGACAT CACCATAGCG GGGCAGAGCG CTGGTGCATC AGCTGCGCAT
 701 CTACTGACTC TTTCTAAAGC TACTGAAGGT CTTTTCAAAA GAGCGATTCT
 751 GATGAGCGGA ACAGGAATGA GCTACTTCTT TACTACTTCT CCACTTTTCG
 801 CGGCCTACAT TTCGAAACAG TTGTTGCAAA TCCTGGGCAA TCAACGAGAC
 851 GGATCCGAAG AAATACATCG GCAGCTCATC GACCTACCCG CAGAGAAACT
 901 GAACGAGGCT AACGCCGTCC TGATTGAACA AATTGGCCTG ACAACCTTCC
 951 TCCCTATTGT GGAATCCCCA CTACCTGGAG TAACAACCAT TATTGACGAT
1001 GATCCAGAAA TCTTAATAGC CGAAGGACGC GGCAAGAATG TTCCACTTTT
1051 AATAGGATTT ACCAGCTCAG AATGCGAGAC TTTCCGCAAT CGACTATTGA
1101 ACTTTGATCT CGTCAAAAAG ATTCAGGACA ATCCTACGAT CATAATACCG
1151 CCTAAACTGT TATTTATGAC TCCACCAGAG CTGTTGATGG AATTAGCAAA
1201 GACTATCGAG AGAAAGTACT ACAACGGTAC AATAAGTATC GATAACTTCG
1251 TAAAATCATG TTCAGATGGC TTCTATGAAT ACCTGCATT GAAACTGGCG
1301 CAAAAACGTG CCGAAACTGG TGGAGCTCCA CTGTACTTGT ACCGGTTCGC
1351 GTACGAGGGT CAGAACAGCA TCATCAAGAA GGTAATGGGG CTGAACCACG
1401 AGGGTGTCGG CCACATTGAG GACTTAACCT ATGTGTTTAA GGTCAACTCT
1451 ATGTCCGAAG CTCTGCACGC ATCGCCTTCT GAGAATGATG TGAAAATGAA
1501 GAATCTAATG ACGGGCTATT TCTTAAATTT TATAAAGTGC AGTCAACCGA
1551 CATGCGAAGA CAATAACTCA TTGGAGGTGT GGCCGGCTAA CAACGGCATG
1601 CAATACGAGG ACATTGTGTC TCCCACCATC ATCAGATCCA AGGAGTTCGC
1651 CTCCAGACAA CAAGACATTA TCGAGTTCTT CGACAGCTTC ACCAGTAGAA
1701 GCCCGCTTGA ATG
```

*FIG. 4*

INSECT SEQUENCES FOR IMPROVING THE EFFICIENCY OF SECRETION OF NON-SECRETED PROTEINS IN EUKARYOTIC CELLS

CROSS-REFERENCE TO RELATED APPLICATIONS

This application claims priority to U.S. Provisional Application Ser. No. 60/056,871 filed Aug. 21, 1997, which is incorporated herein by reference in its entirety.

BACKGROUND OF THE INVENTION

1. Field of the Invention

The present invention relates to the engineering of heterologous gene constructs by recombinant DNA techniques for the more efficient processing and secretion of heterologous genes in eukaryotic cells. Particularly the present invention relates to functionally linking the heterologous gene in frame to the 3' end of the juvenile hormone esterase gene.

2. Description of the Related Art

Recombinant polypeptides for medical, research and veterinary applications are produced using a wide variety of genetically engineered organisms that include transgenic animals (eg. cows, goats) transgenic plants (eg. canola) recombinant viruses (eg. baculoviruses) and transformed prokaryotic cells (eg. bacteria) and eukaryotic cells (eg. yeast and animal cells) in culture.

Since most of the proteins are glycoproteins requiring advanced post-translational modification expression systems using yeast and bacteria are unsuitable. For this reason, other protein expression systems were developed using higher eukaryotes, including virus-based expression systems such as baculovirus and adenovirus and expression from transformed mammalian cells (CHO, BHK NsO etc. and production in the milk of transgenic farm animals). However, even these most advanced vehicles for protein production are inadequate due to difficulties in recovery and purification of the recombinant proteins.

Viral expression systems can produce impressive levels of recombinant proteins in both insect (Maiorella et al. 1988) and mouse cell lines (Garnier et al., 1994) but suffer from serious biological and engineering disadvantages. First, because host cells are killed at the end of each infection cycle, protein expression is only temporary. This also means that protein expression is not suited to the state of the art perfusion bioreactors. Second, the biological authenticity of the expressed protein is not guaranteed because the cell machinery necessary for post-translational modifications is inactivated in the late stages of infection. Unsuitable N-linked glycosylation patterns are widely reported for proteins produced following infection with recombinant viruses, which alters the normal glycosylation characteristics of the cell hosts (Jarvis and Summers, 1989). It is known however that the lepidopteran insect cell hosts are capable of the complex oligosaccharide processing required for in vivo human use of proteins (Davis and Wood 1995) Thirdly, although native genes containing all or part of their introns are generally expressed at a higher level than the corresponding cDNAs (Brinster et al. 1988) virus infected insect cells cannot efficiently excise introns from expressed genomic DNA, thus limiting foreign protein expression from cDNAs only (O'Reilly et al., 1991). Fourth, purification of recombinant proteins from virus infected systems is problematic. Because proteins cannot be secreted efficiently in viral systems due to the inactivation of the secretory pathway upon infection (Jarvis and Summers 1989) they must be recovered from cell lysates after cell lysis. The presence of proteases in such cellular lysates also cause degradation of the over-expressed product.

A major problem in biotechnology exists in the production and recovery of recombinant non-secretion competent polypeptides, such as intracellular proteins or protein subunits, from genetically engineered organisms. Often these intracellular proteins or protein subunits can be expressed at only moderate levels inside a cell and their purification must first include steps to lyse the cells, followed by complex procedures to isolate the desired polypeptides from many other intracellular proteins.

All secreted proteins possess a consensus signal peptide of 10 to 50 amino acids at their N-terminus that directs the protein to the secretory pathway of eukaryotic cells or to the cytoplasmic membrane of prokaryotic cells. Using genetic engineering techniques, some research groups have therefore tried to secrete intracellular proteins by fusing the gene sequences of consensus signal peptides in-frame to the 5' end of the gene encoding the non-secretion polypeptide. When these heterologous genes were expressed, however, the mere presence of a consensus signal peptide was found to be insufficient for the efficient secretion of non-secretion competent polypeptides across a given biological membrane, a problem which is often encountered in the field of biotechnology. For example, Martens et al. (1995), attached the signal sequence of the juvenile hormone esterase gene to the 5' end of the CryIA(b) insecticidal crystal protein gene to induce secretion but found that secretion into the medium from the insect cells was poor.

A method to efficiently secrete non-secretion competent polypeptides, such as cytoplasmic proteins, nuclear factors and protein subunits would be desirable. This would allow the recombinant protein to be expressed at a higher level. Second because the recombinant protein would be secreted into the extracellular environment, purification of the peptide or protein would not be complicated by the presence of other intracellular proteins and would not involve harming the producing cells.

Advantages of the present invention will become apparent from the following description of the invention with reference to the attached drawings.

SUMMARY OF THE INVENTION

The present invention is directed to an expression cassette useful for the secretion of a heterologous protein from eukaryotic cells comprising a DNA sequence encoding a promoter functionally linked to a DNA sequence coding for the juvenile hormone esterase gene which is linked in frame to a gene coding for the heterologous protein.

In a second aspect, the present invention is also directed to a vector useful for the secretion of a heterologous protein from eukaryotic cells comprising an expression cassette comprising a DNA sequence encoding a promoter functionally linked to a DNA sequence coding for the juvenile hormone esterase gene which is linked in frame to a gene coding for the heterologous protein.

In another aspect, the present invention is directed to a method of secreting a heterologous protein, comprising introducing into a cell an expression cassette comprising a DNA sequence encoding a promoter functionally linked to a DNA sequence coding for the juvenile hormone esterase gene which is linked in frame to a gene coding for the heterologous protein under conditions wherein the heterologous protein is expressed and secreted from the cell.

BRIEF DESCRIPTION OF THE DRAWINGS

FIG. 4 shows the DNA [SEQ ID NO: 11] sequence of the juvenile hormone esterase (JHE) gene from *Heliothis virescens*, Genbank Accession No. J04955 (Hanzlik et al., 1989). The first translation start codon, methionine, and the translation stop codon are indicated in bold.

DESCRIPTION OF THE PREFERRED EMBODIMENTS

The present invention relates to an expression cassette useful for the secretion of a heterologous gene from eukaryotic cells comprising a DNA sequence encoding a promoter functionally linked to a DNA sequence coding for the juvenile hormone esterase gene which in turn is functionally linked in frame at its 3' end to a heterologous gene.

The present invention is also directed to a method of secreting a heterologous protein from eukaryotic cells, comprising transforming a cell with a expression cassette comprising a DNA sequence encoding a promoter functionally linked to a DNA sequence coding for the juvenile hormone esterase gene which in turn is functionally linked in frame at its 3' end to a heterologous gene coding for the heterologous protein under conditions wherein the heterologous protein is expressed and secreted as a JHE-fusion protein from the cell.

However, prior to discussing this invention in further detail, the following terms will first be defined.

Definitions

The term "baculovirus" is used herein as an alternative to the term "nuclear polyhedrosis virus" or "NPV". It encompasses viruses classified under subgroup A of the family of Baculoviridae. Preferably, it includes the viruses specific for the following insects: Bombyx sp., Autographica sp., Spodoptera sp. and other lepidoptera.

The term "expression cassette" means a fragment of nucleic acid comprising a promoter sequence and a DNA sequence coding for the juvenile hormone esterase gene which in turn is functionally linked in frame at its 3' end to a gene coding for the heterologous protein, with or without a sequence containing mRNA polyadenylation signals. The expression cassette is capable of directing the expression and secretion of a heterologous protein as a JHE-fusion protein when the expression cassette containing the heterologous protein is introduced into a eukaryotic cell.

The term "vector" means nucleic acid which comprises: (1) the expression cassette, and (2) DNA sequences allowing replication and selection in bacteria, for example *E. coli*. The vector may be a plasmid, another virus or simply a linear DNA fragment. It is contemplated that the vector may be a baculovirus artificial chromosome (BVAC) as set forth in U.S. patent application Ser. No. 09/136,419, entitled BACULOVIRUS ARTIFICIAL CHROMOSOMES AND METHODS OF USE, Attorney Docket No. 028722-171, and filed concurrently herewith, which claims priority to U.S. Provisional patent application Ser. No.60/056,807, filed Aug. 21, 1997, both of which are incorporated by reference herein in their entirety.

The term "baculovirus chromosome" refers to the genome of the baculovirus, which genome is circular. In a preferred embodiment, the baculovirus artificial chromosome is derived from the *B. mori* nuclear polyhedrosis virus. In another embodiment, the chromosome is derived from the *A. californica* nuclear polyhedrosis virus or any other nuclear polyhedrosis virus that contains a lef-8 gene or lef-8-like gene.

Detectable markers are genes which allow detection of cells that have been transfected or infected with the gene. Detectable markers include reporter genes and selection genes. Reporter gene are genes which confer a characteristic onto the cell which is detectable. Suitable reporter genes include the gene encoding for green fluorescent protein, the β-galactosidase gene and the chloramphenicol acetyl transferase gene. Selection genes are wild-type alleles of genes that encode for enzymes which allow the cell to grow on certain media, such as media containing antibiotics. These genes include, for example, the prokaryotic hygromycin resistance and neomycin resistance genes.

The term "juvenile hormone esterase gene" or "JHE gene" means that portion of the juvenile hormone esterase gene, in addition to its signal sequence, which directs the secretion of non-secretion competent heterologous protein when it is functionally linked in frame at its 3' end with the heterologous gene. The juvenile hormone esterase gene does not include its stop codon. The term "JHE gene" means a DNA sequence of at least about 100 bp, more preferably at least about 500 bp and most preferably an entire gene substantially identical to the DNA sequence as set forth in FIG. 4. The juvenile hormone esterase gene is derived from *Heliothis virescens.*

The terms "producing heterologous protein" or "expressing heterologous protein" means that the structural gene encoding the heterologous protein is transcribed into mRNA and that the mRNA is further translated into protein. In a preferred embodiment the heterologous protein will be properly processed by the eukaryotic cell, although such processing may be in a tissue specific manner.

The term "secreting" or "secretion" is the active export of a protein from a cell into the extracellular environment. Generally secretion occurs through a secretory pathway in the cell, for example, in eukaryotic cells, this involves the endoplasmic reticulum and golgi apparatus.

The term "structural gene" refers to those DNA sequences which, when functionally attached to a cellular or viral promoter and linked in frame with the JHE gene, will be transcribed and produce a JHE-heterologous fusion protein which is secreted from the cells.

The term "heterologous structural gene" or "heterologous gene" is a structural gene which will be transcribed and will produce a heterologous protein when functionally attached to any promoter capable of functioning in the host cell or to an enhancer and promoter where the structural gene is introduced into eukaryotic cells either by infection or transfection of cells. While the chloramphenicol acetyl transferase ("CAT") gene was used to characterize the secretion of a heterologous protein under the control of the promoter and the JHE gene in the examples provided herein, it will be recognized that any heterologous structural gene meeting the above criteria may be used in the invention.

Figure 1:
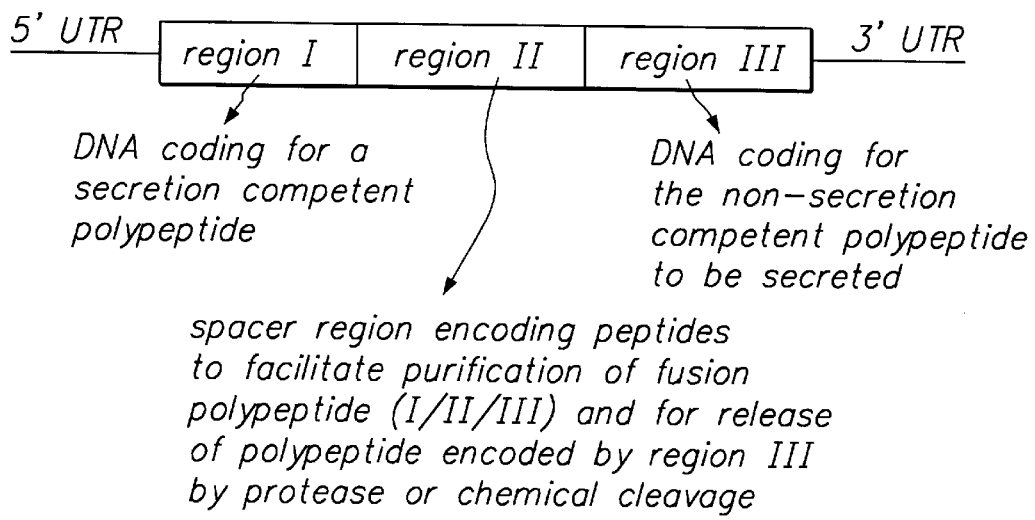
FIG. 1 is the generic design of the DNA molecule for the secretion of either an intracellular protein or protein subunit.

The term "heterologous protein" refers to a protein encoded by a heterologous structural gene. Examples of heterologous proteins are chloramphenicol acetyl transferase, human alpha interferon (IFN-α), insulin-like growth factor-II (IGF-II), human interleukin 3, mouse interleukin 3, human and mouse interleukin 4, human T-lymphotropic virus (HTLV-1) p40$^x$, HTLV-1 env, human immunodeficiency virus (HIV-1) gag, pol, sor, gp41, and gp120, adenovirus Ela, Japanese encephalitis virus env (N), bovine papilloma virus 1 (BPV1) E2, HPV6b E2, BPV1 E6, and human apolipoproteins A and E; β-galactosidase, hepatitis B surface antigen, HIV-1 env, HIV-1 gag, HTLV-1 p40$^x$, human IFN-β, human interleukin 2, c-myc, *D. melanogaster* Kruppel gene product, bluetongue virus VP2 and VP3, human parainfluenza virus hemagglutinin (HA), influenza polymerases PA, PB1, and PB2, influenza virus HA, lymphocytic choriomeningitis virus (LCMV) GPC and N proteins, *Neurospora crassa* activator protein, polyomavirus T antigen, simian virus 40 (SV40) small t antigen, SV40 large T antigen, Punta Toro phlebovirus N and Ns proteins, simian rotavirus VP6, CD4 (T4), human erythropoietin, Hantaan virus structural protein, human epidermal growth factor (EGF) receptor, human insulin receptor, human B lymphotrophic virus 130-kd protein, hepatitis A virus VP1, human tyrosine hydroxylase, human glucocerebrosidase, p53 protein, topoisomerases, ecdysone receptor, DNA polymerase subunits, RNA polymerase I, II and III subunits, cytoplasmic and nuclear factors.

The term "non-secretion competent heterologous proteins" means proteins which are not naturally secreted from the cell into the extracellular environment. Examples of non-secretion competent heterologous proteins are chloramphenicol acetyl transferase, human immunodeficiency virus (HIV-1) gag, pol, sor, β-galactosidase, c-myc, influenza polymerases PA, PB1, and PB2, *Neurospora crassa* activator protein, p53 protein, topoisomerases, ecdysone receptor, DNA polymerase subunits, RNA polymerase I, II and III subunits, cytoplasmic and nuclear factors and non-secretion competent subunits of secreted proteins.

The term "promoter" means a DNA sequence which initiates and directs the transcription of a heterologous gene into an RNA transcript in cells. The promoter may be a baculovirus promoter derived from any of over 500 baculoviruses generally infecting insects, such as for example the orders Lepidoptera, Diptera, Orthoptera, Coleoptera and Hymenoptera, including for example but not limited to the viral DNAs of *Autographa californica MNPV*, *Bombyx mori NPV*, *Tricoplusia ni MNPV*, *Rachiplusia ou MNPV*, or *Galleria mellonella MNPV* wherein said baculovirus promoter is a baculovirus immediate-early gene IE1 or IEN promoter; a delayed-early gene promoter region such as the 39K gene promoter or a baculovirus late gene promoter, such as the polyhedrin gene promoter. The promoter may also be a insect cellular promoter, such as the actin gene promoter, the ribosomal gene promoter, the histone gene promoter, or the tubulin gene promoter. The promoter may also be a mammalian promoter such as the cytomegalovirus immediate early promoter, the SV40 large T antigen promoter or the Rous Sarcoma virus (RSV) LTR promoter.

The term "enhancer" means a cis-acting nucleic acid sequence which enhances the transcription of the structural gene and functions in an orientation and position-independent manner. The enhancer can function in any location, either upstream or downstream relative to the promoter. The enhancer may be any DNA sequence which is capable of increasing the level of transcription from the promoter when the enhancer is functionally linked to the promoter, for example the RSV LTR enhancer, baculovirus HR1, HR2 or HR3 enhancers or the CMV immediate early gene product enhancer. In a preferred embodiment, the enhancer is the 1.2 kb BmNPV enhancer fragment set forth in U.S. patent application Ser. No. 08/608,617, now U.S. Pat. No. 5,759,809, which is incorporated by reference herein.

It is also contemplated that the expression of the heterologous gene may be enhanced by the expression of other factors, for example the IE-1 protein of nuclear polyhedrosis viruses or the herpes simplex virus VP16 transcriptional activator.

The term "functionally linked" or "functionally attached" when describing the relationship between two DNA regions simply means that they are functionally related to each other and they are located on the same nucleic acid fragment. A promoter is functionally attached to a structural gene if it controls the transcription of the gene and it is located on the same nucleic acid fragment as the gene. An enhancer is functionally linked to a structural gene if it enhances the transcription of that gene and it is functionally located on the same nucleic acid fragment as the gene.

The term "linked in frame" means that one gene is linked at its 3' end to the 5' end of a second gene such that after transcription and translation of the genes a single fusion protein comprising the two proteins encoded by the genes is produced. The two genes may be linked by a spacer nucleic acid sequence.

The term "introduction" refers to either infection or transfection of insect cells.

The term "infection" refers to the invasion by pathogenic viral agents of cells where conditions are favorable for their replication. Such invasion can occur by placing the viral particles directly on the insect cell culture or by injection of the insect larvae with the recombinant virus or by oral ingestion of the viral particles by the insect. The amount of recombinant virus injected into the larvae will be from $10^2$ to $10^5$ pfu of non-occluded virus/larvae. Alternatively, larvae can be infected by the oral route using occlusion bodies carrying recombinant viruses. In general, the amount of occlusion bodies fed to the larvae is that amount which for wild-type viruses corresponds to the $LD_{50}$ for that species of baculovirus and insect host. The $LD_{50}$ varies with each species of baculovirus and the age of the larvae. One skilled in the art can readily determine the amount of occlusion bodies to be administered. Typically, the amount will vary from $10-10^6$ occlusion bodies/insect.

The term "transfection" refers to a technique for introducing purified nucleic acid into cells by any number of methods known to those skilled in the art. These include but are not limited to, electroporation, calcium phosphate precipitation, lipofection, DEAE dextran, liposomes, receptor-mediated endocytosis, and particle delivery. The chromosomes or DNA can also be used to microinject eggs, embryos or ex vivo or in vitro cells. Cells can be transfected with the chromosomes or with the DNA described herein using an appropriate introduction technique known to those in the art, for example, liposomes. In a preferred embodiment, the DNA is introduced into the insect cells by mixing the DNA solution with "Lipofectin" (GIBCO BRL Canada, Burlington, Ontario) and adding the mixture to the cells.

The cell or host cell may be prokaryotic or eukaryotic. If the cell is eukaryotic, it is preferably an insect cell or a mammalian cell.

The term "insect cells" means insect cells from the insect species which are subject to baculovirus infection. For example, without limitation: *Autographa californica; Bombyx mori; Spodoptera frugiperda; Choristoneura fumiferana; Heliothis virescens; Heliothis zea; Helicoverpa zea; Helicoverpa virescens; Orgyia pseudotsugata; Lymantria dispar; Plutella xylostella; Malacostoma disstria; Trichoplusia ni; Pieris rapae; Mamestra configurata; Mamestra brassica; Hyalophora cecropia.*

The term "mammalian cells" includes, for example, COS cells, CHO cells, BHK cells and HeLa cells.

Methodology

Signal peptide sequences are often not sufficient for the efficient secretion of certain peptides or proteins such a nuclear factors from eukaryotic cells. Such peptides or proteins are termed non-secretion competent proteins.

It has now been found that the fusion of the JHE gene to the 5' end of the non-secretion competent protein will allow efficient secretion of the fusion protein from the cell into the extracellular environment. In order to achieve continuous high level secretion of heterologous proteins in cells, the cells are transformed with an expression cassette comprising a promoter functionally linked to the JHE gene which in turn is linked in frame to the gene coding for the heterologous protein. The linkage of the JHE gene to the heterologous gene is preferably in frame to ensure that both the JHE gene and the heterologous gene are transcribed and translated as a single fusion protein.

To achieve continuous secretion of heterologous proteins, in one embodiment, normal insect tissue culture cells can be transformed with a vector containing such an expression cassette comprising a promoter and the JHE gene functionally linked in frame to the desired heterologous gene. It is contemplated that the vector may also contain an extra gene expressing a selective marker (e.g. antibiotic resistance gene under the control of a promoter that functions constitutively in insect cells). Application of a relevant selection should lead to integration of one or more multiple copies of the plasmid into the chromosomes of the cells, thus generating an insect cell line capable of continuous secretion of the heterologous protein.

It is contemplated that the expression cassette may also include an enhancer sequence which would increase the level of transcription from the promoter. The level of transcription from the cellular promoter functionally linked to an enhancer as compared to the level of transcription from the cellular promoter alone is preferably at least about 10 fold and more preferably at least about 100 fold.

The insect cells may further express other transcription factors which enhance transcription such as the IE-1 protein. In one embodiment the insect cells can be transformed with a vector containing the IE-1 gene and a suitable resistance/selectable marker gene. Application of a relevant selection should lead to integration of one or more multiple copies of the vector into the chromosomes of the cells, thus generating an insect cell line capable of continuous high level expression of the IE-1 gene product. Thus the cell line will contain the IE-1 gene in the absence of added baculovirus. Such a cell line can be subsequently transformed with additional vectors containing either the expression cassette containing an insect cellular promoter functionally linked to the JHE gene and a heterologous gene. The second vector may also comprise an additional gene conferring resistance to a second selection agent. In another embodiment, the gene for the IE-1 protein may be inserted into the vector comprising the expression cassette such that the vector contains both the JHE-heterologous genes and the IE-1 gene. In both cases, synthesis of the foreign protein will be continuous, because integrated expression cassettes cannot be lost through replication and the insect cells never die because they are not infected by any viruses. The level of production of heterologous proteins in cells expressing the IE-1 gene as compared to cells without the IE-1 gene is preferably at least about 10 fold greater and more preferably at least about 100 fold greater.

The vector may be a baculovirus artificial chromosome as set forth in U.S. patent application No. Ser. No. 60/056,807, entitled BACULOVIRUS ARTIFICIAL CHROMOSOMES AND METHODS OF USE, Attorney Docket No. 028722-153, filed Aug. 21, 1997 and incorporated by reference in its entirety. Such baculovirus artificial chromosomes would not integrate into the cellular chromosomes but rather replicate autonomously without killing the cells.

It is appreciated that the expression cassette of the present invention could be used to express and secrete any heterologous protein. However, the expression cassette is particularly useful in the expression and secretion of heterologous proteins previously thought to not be secretion competent.

Eukaryotic cells, other than insect cells could be transfected with the expression cassette of the present invention, resulting in the expression and secretion of the heterologous protein from the eukaryotic cell. In particular it is contemplated that mammalian tissue culture cells could be used for the expression and secretion of heterologous proteins. If mammalian cells were used, the promoter sequence and enhancer sequence would preferably be those promoters and enhancers appropriate for expression of the heterologous gene in the mammalian cells.

The heterologous protein is secreted from the cell into the extracellular environment as a fusion protein, wherein the heterologous protein may be fused in frame directly, or via a linking peptide, to the 3' end of the JHE gene. The heterologous fusion protein may then be treated to remove the JHE protein sequences at the 5' end resulting in an active heterologous protein. In order to facilitate the removal of the JHE protein sequences, it is contemplated that the heterologous gene may be linked to the JHE gene in frame via a linking sequence which encodes an amino acid sequence or linking peptide which can be easily cleaved. An example of a suitable cleavage site is the nucleic acid sequence coding for the amino acid sequence (residues 11–15 of [SEQ ID NO: 10] which is a cleavage site recognized by the protease porcine intestine enteropeptidase.

The linking sequence may also contain a DNA sequence encoding a spacer peptide for better access to the cleavage site. The linking sequence may also contain a sequence for efficient purification of the fusion peptide from the extracellular environment. An example of such a sequence is a nucleic acid sequence coding for six histidine residues, which residues will bind to a Ni(II)-NTA chromatography matrix for affinity purification.

Utility

This technique would be useful for the extracellular production of non-secretion competent polypeptides from a genetically engineered organism for medical, research or veterinary application. For polyclonal or monoclonal antibody generation, this secretion technique would be coupled with a DNA vaccine vector to induce a humoral immune response against non-secretion competent polypeptides. For non-secretion competent polypeptides derived from pathogenic organisms, this secretion technique would be coupled with a DNA vaccine vector to induce an immune response for human and animal vaccines.

As can be appreciated from the disclosure above, the present invention has a wide variety of applications.

Accordingly, the following examples are offered by way of illustration and not by way of limitation.

EXAMPLES

In the examples below, the following abbreviations have the following meanings. If not defined below, then the abbreviations have their art recognized meanings.

ORF—open reading frame
kb—kilobase
mg—milligram
mL—milliliter

Chemicals used in the following examples were obtained from the following companies:

Amersham Canada Ltd., Oakville, Ontario, Canada
J. T. Baker, Phillipsburg, N.J.
BioRad Laboratories Ltd. Canada, Mississauga, Ontario, Canada
Boehringer Mannheim, Laval, Quebec, Canada
5 Prime-3 Prime, Inc., Boulder, Colo.
GIBCO BRL Canada, Burlington, Ontario, Canada
Hyclone Laboratories, Inc., Logan, Utah
ICN Biopharmaceuticals Canada Ltd., Montreal Quebec, Canada
JRH Biosciences, Inc., Lenexa, Kans.
Life Technologies, Burlington, Ontario, Canada
New England Biolabs, Inc., Mississauga, Ontario, Canada
Pharmacia LKB, Baie d' Urfe', Quebec, Canada
Promega Corporation, Madison, Wis.
Sigma, St. Louis, Mo.
Stratagene, La Jolla, Calif.
United States Biochemicals, Cleveland, Ohio All enzymes used for the construction and characterization of the recombinant plasmids and baculoviruses were obtained from Pharmacia, LKB; New England Biolabs, Inc.; GIBCO BRL Canada; Boehringer Mannheim; and used according to those suppliers recommendations.

The cloning procedures set forth in the examples are standard methods described in Sambrook et al., *Molecular Cloning: A Laboratory Manual*, Cold Spring Harbor Laboratory (1989) which is incorporated herein by reference. This reference includes procedures for the following standard methods: cloning procedures with *E. coli* plasmids, transformation of *E. coli* cells; plasmid DNA purification, agarose gel electrophoresis, restriction endonuclease digestion, ligation of DNA fragments and other DNA-modifying enzyme reactions.

Example 1
Secretion of Chloramphenicol Acetyl Transferase (CAT)

Figure 2A:
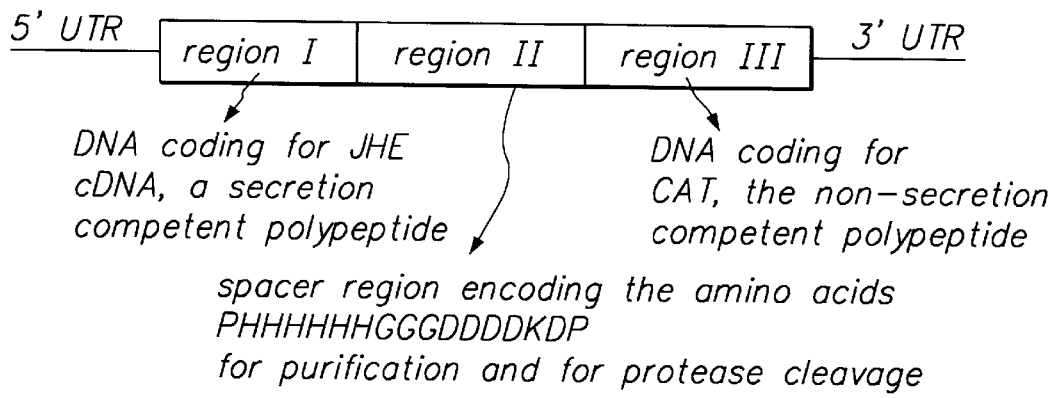
FIG. 2A [SEQ ID NO: 10] is the design of the DNA module used to secrete the bacterial cytoplasmic protein CAT.

The DNA module for the secretion of chloramphenicol acetyl transferase (CAT) is shown in FIG. 2A. At the 5' end, it contains the complete cDNA coding for the insect secreted protein juvenile hormone esterase (JHE) (Hanzlik et al.) which can be secreted from animal cell hosts. The spacer region contains DNA coding for six histidine residues that are attracted to Ni(II)-NTA chromatography matrices for affinity purification (Kroll 1993). The spacer region also contains a nucleic acid sequence coding for the amino acid sequence DDDDK (residues 11–15 of SEQ ID NO: 10), which is a cleavage site recognized by the protease porcine intestine enteropeptidase (Kell 1971). The spacer region is bound on each side by a proline residue which encourages the spacer peptide to form its own domain for better access to both the chromatographic purification matrix and the enteropeptidase. The module also contains the DNA sequence coding for CAT.

The vectors for Example 1 were constructed as follows. The expression plasmid pIE1/153A contains the *Bombyx mori* cytoplasmic actin cassette (Johnson et al., 1992; U.S. patent application Ser. No. 08/608,617, now U.S. Pat No. 5,759,809), *Bombyx mori* Nuclear Polyhedrosis Virus (BmNPV) HR3 enhancer element and the BmNPV ie1 gene and was constructed as follows. A 1.2 kb SspI fragment corresponding to the BmNPV genomic region from 51.8 to 52.7 map units containing the BmNPV HR3 element was cloned into the SmaI site of pBluescript-SK+ (Stratagene) to yield plasmid p153. The plasmid pIE1/153 was made by inserting a 3.8 kb ClaI fragment containing the ie1 gene into the ClaI site of plasmid p153, removing unwanted restriction sites in the polylinker of this plasmid by double digestion with SacII and BamHI, blunt ending with T4 DNA polymerase and self-ligating the resultant plasmid. A 2.2 kb SacI fragment containing the actin cassette from the plasmid pBmA (Johnson et al., 1992) was ligated into the unique SacI site of plasmid pIE1/153 to yield the expression plasmid pIE1/153A.

The vector, pBmA is a pBluescript (Stratagene) derivative of clone pA3-5500 which contains the A3 cytoplasmic actin gene of *Bombyx mori* (Mounier and Prudhomme, 1986). Plasmid pBmA was constructed to contain 1.5 kb of the A3 gene 5' flanking sequences and part of its first exon to position +67 (relative to transcription initiation), a polylinker region derived from plasmid pBluescript (Stratagene) for insertion of foreign gene sequences, and an additional 1.05 kb of the A3 gene sequences encompassing part of the third exon of the gene from position +836 and adjacent 3' flanking sequences which contain signals required for RNA transcript polyadenylation. See U.S. patent application Ser. No. 08/608,617, now U.S. Pat. No. 5,759,809, which is incorporated by reference herein in its entirety.

This expression vector was constructed by (1) subcloning into plasmid Bluescript-SK+ (Stratagene) a 1.5 kb KpnI/AccI fragment of clone pA3-5500 containing the 5' flanking, 5' untranslated and coding sequences of the A3 gene up to position +67 to generate plasmid pBmAp; (2) mutagenizing the ATG translation initiation codon present at position +36 to +38 of the actin coding sequence in plasmid pBmAp into AGG, AAG or ACG by the method of Kunkel (1985) to generate plasmids pBmAp.AGG, pBmAp.AAG and pBmAp.ACG; (3) subcloning into plasmid pSP72 (Promega Corporation) a 1.05 kb XhoI/SalI fragment of clone pA3-5500, containing part of the third exon of the actin gene from position +836 and adjacent 3' flanking sequences which include signals required for RNA transcript polyadenylation, to generate plasmid pBmAt; (4) converting the unique XhoI site of plasmid pBmAt into a NotI site by digestion of this plasmid with XhoI (GIBCO BRL), and end-filling with Klenow DNA polymerase (Boehringer Mannheim), ligation of NotI linkers (DNA Synthesis Laboratory.

A 0.8 kb BamHI fragment, containing the CAT open reading frame was isolated from pBmA.CAT (Johnson et al., 1992; U.S. Pat. No. 08/608,617) and cloned into the unique BamHI site in pIE1/153A to generate pIE1/153A.CAT.

A 1.8 kb EcoRI fragment containing the JHE(kk) open reading frame was first isolated from pAcUW21-KK (Bonning and Hammock, 1996), NotI linkers were ligated to its ends, and it was inserted into the unique NotI site of pIE1/153A to generate the plasmid pIE1/153A.JHE.

The plasmid pIE1/153A.JHE.HisEP.CAT was generated in several steps.

(i) First 2 oligonucleotides [SEQ ID NOs: 1 and 2] were synthesized (5' to 3') coding for region II in FIG. 2A:
I. 5'-AAAGGATCCAATGCCACATCATCATCAT CATCATGGCGGCGGC-3'
II. 5'-AAAACCATGGCCTGGGTCCTTGTCGTCGTC GTCGCCGCCGCC-3'

These oligonucleotides were annealed together, end-filled by mutually primed synthesis with Klenow enzyme, double digested with BamHI and NcoI, and ligated into pBluescript-SK+ (Stratagene) to yield pHisEP(NcoI).

(ii) Next two mutagenic primers [SEQ ID NOs: 3 and 4] (5' to 3') were synthesized in order to generate region III in FIG. 2A:
I. 5'-GGGCTACCATGGAGAAAAAAATCACTGG-3'
II. 5'-GGGTGCTCTAGAATTTCTGCCATTCATCC-3'

PCR amplification using Pfu polymerase from pIE1/153A.CAT plasmid DNA yielded a 0.8 kb product containing the CAT open reading frame that was double digested with NcoI and XbaI and ligated in-frame into the unique NcoI/XbaI sites of pHisEP(NcoI) to yield pHisEP.CAT.

(iii) The following two mutagenic primers [SEQ ID NOs: 5 and 6] (5' to 3') were synthesized to obtain region I in FIG. 2a:
I. 5'-AAAAGGATCCATGACTTCACACGTACTCGC-3'
II. 5'-AAAAGGATCCTTCAAGCGGGCTTCTACTG-3'

PCR amplification using Pfu polymerase from pIE1/153A.JHE(kk) plasmid DNA yielded a 1.6 kb product containing the JHE open reading frame (with no stop codon) that was partially digested with BamHI and ligated in-frame into the unique BamHI site of pHisEP.CAT to yield pJHE.HisEP.CAT.

(iv) A partial BamHI digestion and complete NotI digestion of pJHE.HisEP.CAT released a 2.5 kb fragment containing the complete secretion module (regions I, II, and III in FIG. 2A) that was ligated into the unique BamHI/NotI sites of the expression plasmid pIE1/153A to yield pIE1/153A.JHE.HisEP.CAT.

Figure 2B:
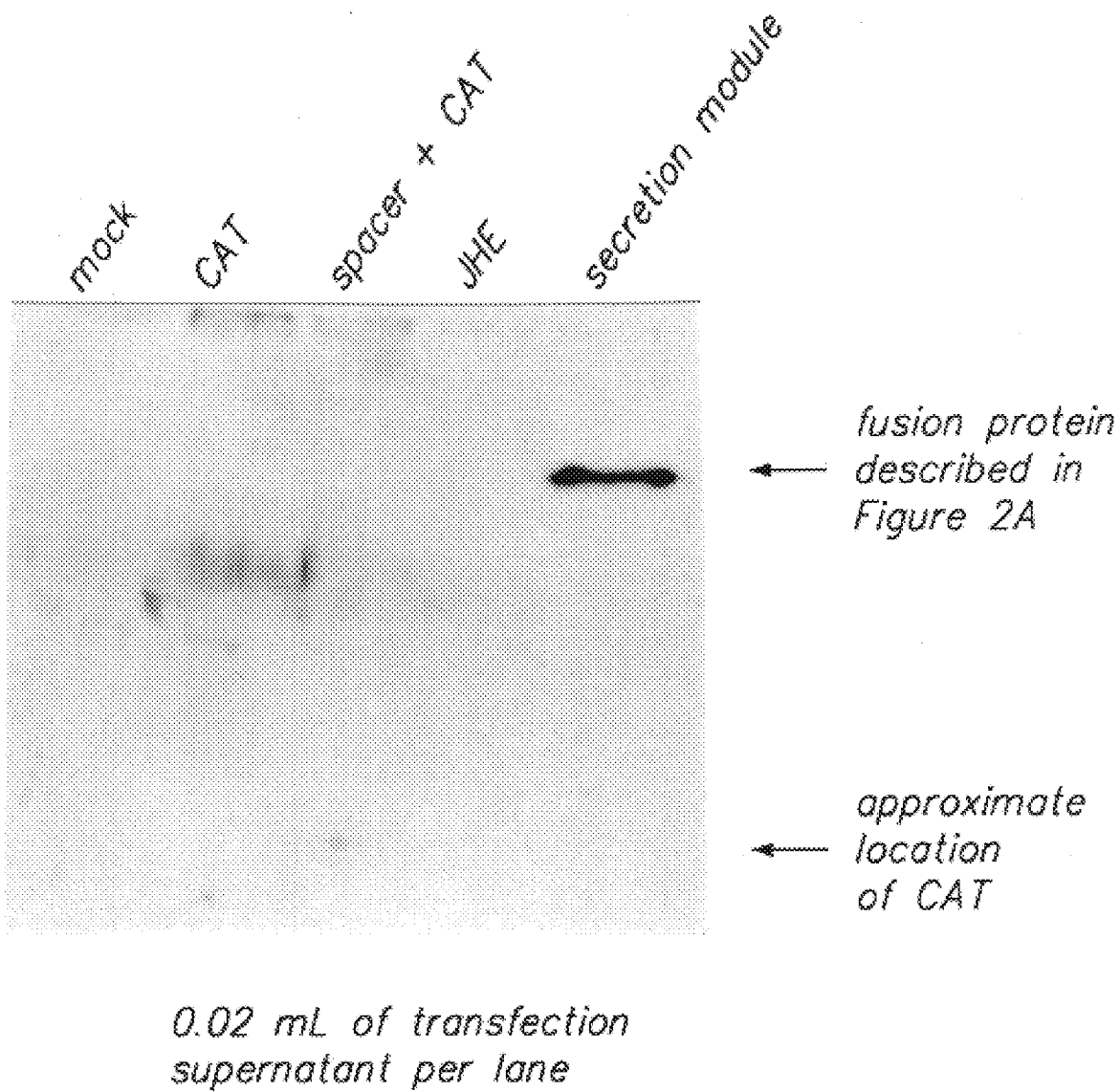
FIG. 2B is a western blot which shows the secretion of the JHE-CAT fusion protein using the secretion module described in FIG. 2A.

Control DNA for the experimental demonstration of the secretion of CAT was the expression plasmid pIE1/153A ("mock DNA"); the expression plasmid with the complete CAT gene pIE1/153A.CAT ("CAT"), the expression plasmid with spacer plus the CAT gene ("spacer+CAT") and the expression plasmid with the JHE gene pIE1/153A.JHE ("JHE") in FIG. 2B.

The various expression plasmids were transfected into *Bombyx mori* insect host cells in in vitro cultures. (Lu et al. 1996) Bm5 cells were maintained in IPL-41 (Gibco)+10% fetal bovine serum. For transfection, cells were seeded into 35 mm diameter dishes at a density of $10^5$ cells/well, allowed to adhere, and transfected with 0.5 mL of basal media containing 3 micrograms plasmid DNA and 15 microgram Lipofectin (Gibco) for 5 hours according to manufacturers instructions. Cells and supernatant were harvested for analysis 2 days following transfection.

The extracellularly expressed CAT was detected by western blotting (Sambrook 1989) the culture supernatants, using an antibody recognizing CAT. Aliquots of cells or cell culture supernatants were resolved by electrophoresis in a SDS-containing 8% polyacrylamide gel (SDS-PAGE) and electroblotted onto Hybond-ECL membrane (Amersham). After transfer, the membrane was blocked for 1 hour at room temperature in 50 ml PBS-0.1% Tween-20 (PBST) containing 10% (w/v) skim milk powder (PBSTM). The filter was incubated for 1 hour at room temperature in 5 mL PBSTM containing rabbit polyclonal anti-CAT antibody (5 Prime-3 Prime, Inc., 1:1000 dilution), washed twice for 15 minutes with PBST, and incubated 1 hour with 5 mL PBSTM containing horseradish peroxidase conjugated goat anti-rabbit IgG (Life Technologies; 1:1000 dilution). After washing twice with PBST, the filter was incubated with ECL chemiluminescent substrate (Amersham) according to the suppliers' instructions and exposed to X-ray film.

FIG. 2B shows that no CAT was detected in either the supernatant of cells transfected with mock plasmid DNA or cells transfected with a plasmid expressing CAT or cells transfected with a plasmid expressing the spacer plus the CAT gene, or cells transfected with a plasmid expressing JHE. CAT was detected in the supernatant of cells transfected with plasmid pIE1/153A.JHE.HisEP.CAT ("secretion module"). Therefore, the naturally secreted protein JHE can be employed to drag a non-secretion competent polypeptide, such as CAT, into an extracellular environment.

Example 2
Liberation of the CAT Peptide from the Fusion Protein

Figure 2C:
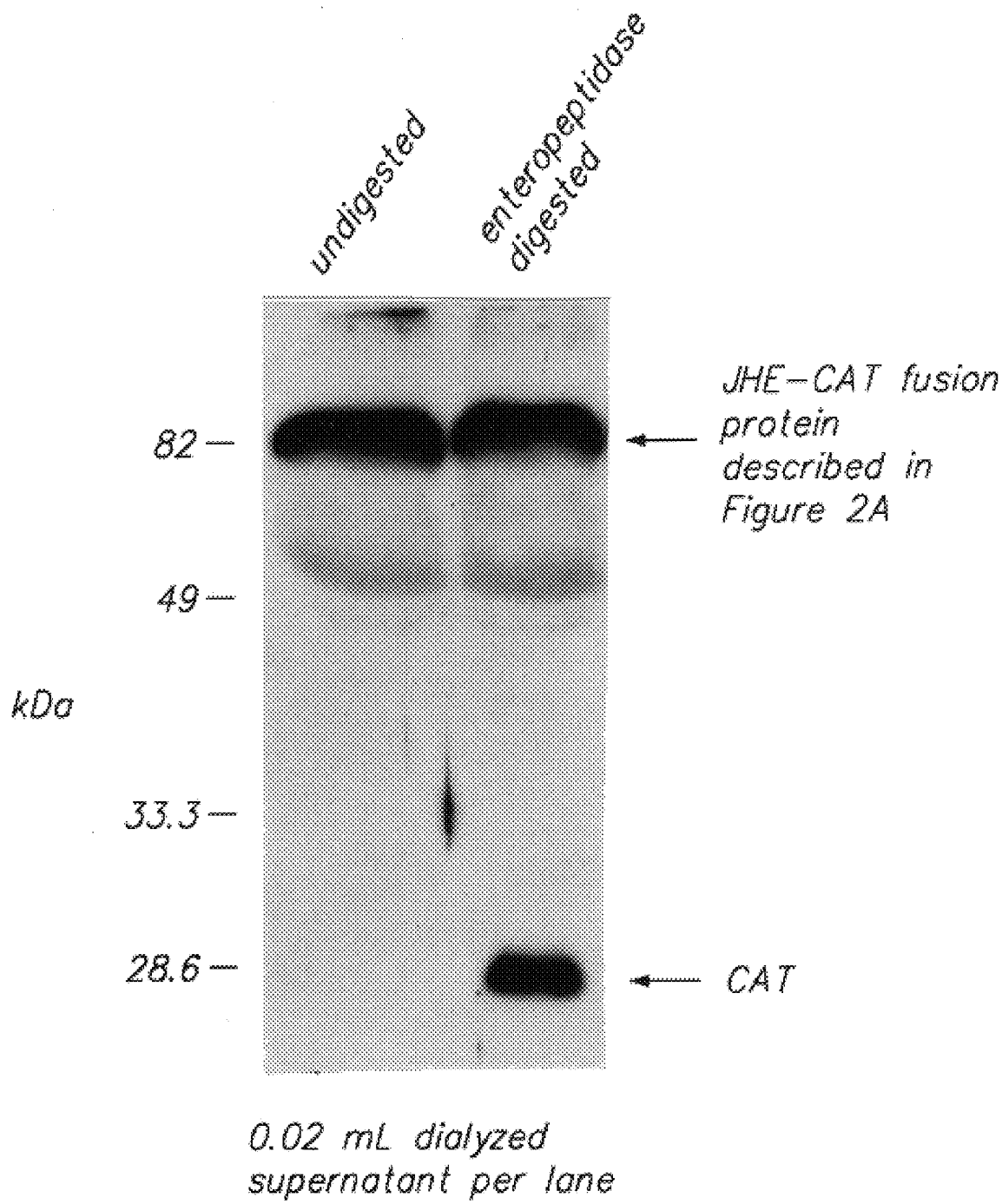
FIG. 2C shows the liberation of the CAT protein from the fusion protein when incubated with enteropeptidase.

To demonstrate that the CAT protein could be liberated from the expressed fusion protein culture, supernatant from the culture described in Example 1 was dialyzed against enteropeptidase buffer, and incubated with porcine intestine enteropeptidase [ICN Biopharmaceuticals Canada Ltd.] for 36 hours at 37° C. (Kell 1971). FIG. 2C is a western blot of an enteropeptidase digested sample, using the anti-CAT antibody (5 Prime-3 Prime, Inc. 1:1000 dilution) which shows that some CAT was successfully liberated from the fusion protein.

Example 3
Secretion of BmCF1

The intracellular protein *Bombyx mori* chorion factor 1 (BmCF1) is naturally found in the nucleus of some *Bombyx mori* insect cells. The module for secretion of BmCF1 is shown in FIG. 3A.

A 3.8 kb NotI fragment of pBmCFI (Tzertziniz et al, 1994) containing the BmCF1 open reading frame was ligated into the unique NotI site of pIE1/153A to form pIE1/153A.BmCF1.

The plasmid pIE1/153A.JHE.HisEP.BmCF1 was generated in several stages.

Figure 3A:
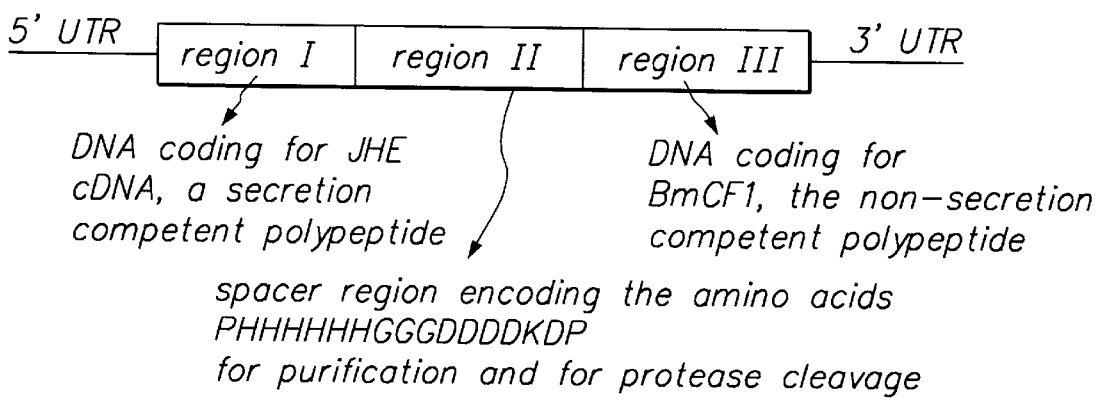
FIG. 3A [SEQ ID NO: 10] shows the design of the DNA molecule used to secrete the insect nuclear protein BmCF1.

(i) First 2 oligonucleotides [SEQ ID NOs: 8 and 9] were synthesized (5' to 3') coding for region II in FIG. 3A:
I. 5'-AAAGGATCCA ATG CCA CAT CAT CAT CAT CAT CAT GGC GGC GGC-3'
II. 5'-AAAAGC ATG CCC TGG GTC CTT GTC GTC GTC GTC GCC GCC GCC-3'

These oligonucleotides were annealed together, endfilled by mutually primed synthesis with Klenow enzyme, double digested with BamHI and SphI and ligated into pBluescript-SK+ (Stratagene) to yield pHisEP (SphI).

(ii) The following 2 oligonucleotides [SEQ ID NOs: 8 and 9] were synthesized (5' to 3') to obtain region III in FIG. 3A:
I. 5'-TGTGGGCATGCAGAGCGTGGCGAAG-3'
II. 5'-CGACATTCAAATCTAGAATAAGTCCCCCTAC-3'

PCR amplification using Pfu polymerase from pBmCF1plasmid DNA yielded a 1.5 kb product containing the BmCF1 open reading frame that was completely digested with XbaI and partially digested with SphI and ligated in-frame into the unique SphI/XbaI sites of pHisEP (SphI) to yield pHisEP.BmCF1.

(iii) The PCR product containing the JHE ORF (with no stop codon), described in Example 1, was ligated in-frame into the unique BamHI site of pHisEP.BmCF1 to yield pJHE.HisEP.BmCF1.

(iv) A partial BamHI digestion and complete NotI digestion of pJHE.HisEP.BmCF1 released a 2.6 kb fragment containing the complete secretion module (regions I, II and III in FIG. 3A) that was ligated into the unique BamHI/NotI sites of pIE1/153A to yield pIE1/153A.JHE.HisEP.BmCF1.

Figure 3B:
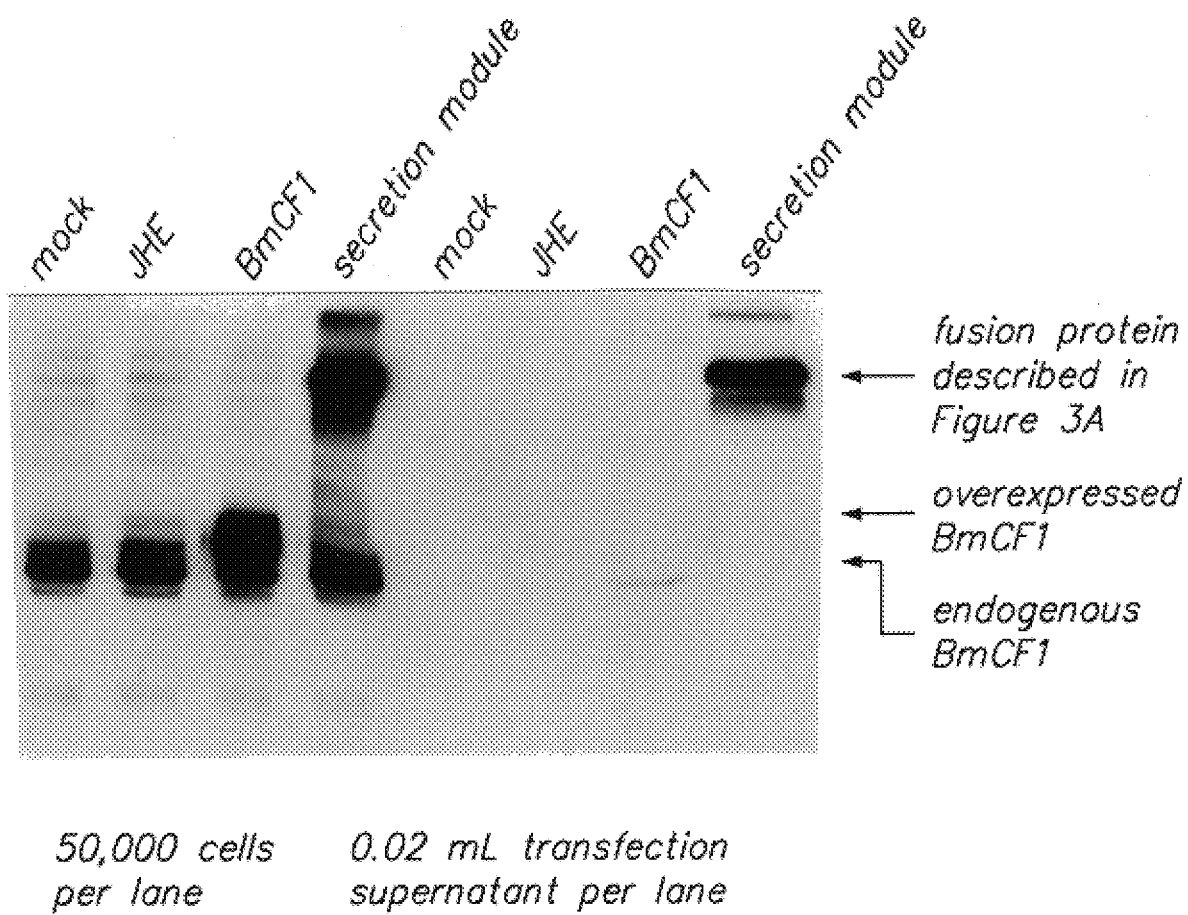
FIG. 3B is a western blot which shows the secretion of the JHE-BmCF1 fusion protein using the secretion module described in FIG. 3A.

Control DNA for the experimental demonstration of the secretion of BmCF1 was the expression plasmid pIE1/153A ("mock DNA"); the expression plasmid with the complete BmCF1 gene, pIE1/153A.BmCF1 ("BmCF1"), and the expression plasmid with the complete JHE gene, pIE1/153A.JHE ("JHE") in FIG. 3B.

Each plasmid was transfected into *Bombyx mori* insect host cells in in vitro cultures as set forth in Example 1. Intracellular and extracellular expressed BmCF1 was detected by western blotting using mouse monoclonal anti-BmCF1 (provided by Dr. F. C. Kafatos, Harvard University, Boston, Mass.; 1:100 dilution) and horse-radish peroxidase conjugate goat anti-mouse antibody [Life Technologies; 1:1000 dilution] by the methods set forth in Example 1.

The western blot, shown in FIG. 3B reveals that the normally intracellular protein BmCF1 was only detected in the supernatant of cells transfected with the pIE1/153A.JHE.HisEP.BmCF1, ("secretion module") described in FIG. 3A.

While the present invention has been described with reference to what are considered to be the preferred examples, it is to be understood that the invention is not limited to the disclosed examples. To the contrary, the invention is intended to cover various modifications and equivalent arrangements included within the spirit and scope of the appended claims.

REFERENCES

All publications, patents and patent applications are herein incorporated by reference in their entirety to the same extent as if each individual publication, patent or patent application was specifically and individually indicated to be incorporated by reference in its entirety.

U.S. patent application Ser. No. 08/608,617

Bonning and Hammock, (1996) *Ann. Rev. Entomol.* 41:191–210

Brinster et al., (1988) *Proc. Natl. Acad. Sci.* U.S.A. 85:836–840

Davis and Wood (1995) "Intrinsic glycosylation potentials of insect cell cultures and insect larvae" in vitro Cell. Dev. Biol.

Garnier et al., (1994) *Cryotech* 15(1–3):145–155

Hanzlik et al., (1989) *J. Biol. Chem.*264:12419–12425

Huybrechts et al. (1992) "Nucleotide sequence of a trans-activating *Bombyx mori* nuclear polyhedrosis virus immediate early gene" *Biochim. Bioph. Acta.* 1129:328–330

Jarvis and Summers, (1989) "Glycosylation and secretion of human tissue plasminogen activator in recombinant baculovirus-infected cells." Mol Cell Biology 9:214–223

Johnson et al., (1992) "A cellular promoter-based expression cassette for generating recombinant baculoviruses directing rapid expression of passenger genes in infected insects" *Virology* 190:815–823

Kell (1971) in *The Enzymes*, Academic Press, 3:249–275

Kroll et al., (1993) *DNA and Cell Bio.* 12:441–453

Kunkel (1985) *Proc. Nat. Acad. Sci* U.S.A. 82:488–492

Lu et al., (1996)"trans-activation of a cell housekeeping gene promoter by the IE1 gene product of baculoviruses" *Virology* 218:103–113

Maiorella et al. (1988) "Large scale insect culture media for recombinant protein production" *Bio/Technology* 6:1406–1410

Martens et al., (1995) "Characterization of baculovirus insecticides expressing tailored *Bacillus thuringiensis* CryIA (b) crystal proteins" *J. of Invertebrate Pathology* 66:249–157

Mounier and Prudhomme, (1986) *Biochimie* 68:1053–1061

O'Reilly et al., (1992) *Baculovirus Expression Vectors.* W. H. Freeman and Co.

Sambrook et al., (1989) In *Molecular Cloning, A laboratory Manual Cold* Spring Harbor Press.

Tzertziniz et al, (1994) *J. Mol. Biol.* 238:479–486

What is claimed is:

1. An expression cassette for the secretion of a heterologous protein from eukaryotic cells comprising a DNA sequence encoding a promoter functionally linked to a DNA sequence coding for a juvenile hormone esterase which is linked in frame to a gene coding for the heterologous protein.

2. The expression cassette of claim 1 wherein the promoter is selected from the group consisting of a viral promoter, an insect cellular promoter and a mammalian promoter.

3. The expression cassette of claim 1 further comprising a DNA sequence encoding an enhancer functionally linked to the promoter.

4. The expression cassette of claim 1 wherein the juvenile hormone esterase gene is linked in frame to the gene encoding the heterologous protein by a linking sequence.

5. A cell transformed with the expression cassette of claim 1.

6. The expression cassette of claim 2, wherein the enhancer is a viral enhancer.

7. A vector for the secretion of a heterologous protein from eukaryotic cells comprising an expression cassette comprising a DNA sequence encoding a promoter functionally linked to a DNA sequence coding for a juvenile hormone esterase which is linked in frame to a gene coding for the heterologous protein.

8. The vector of claim 7 wherein the promoter is selected from the group consisting of a viral promoter, an insect cellular promoter and a mammalian promoter.

9. The vector of claim 7 further comprising a DNA sequence encoding an enhancer functionally linked to the promoter.

10. The vector of claim 7, further comprising a selectable marker gene.

11. The vector of claim 9, wherein the enhancer is a viral enhancer.

12. The cell of claim 5 wherein the cell is a eukaryotic cell.

13. A method of secreting a heterologous protein, comprising introducing into a cell an expression cassette comprising a DNA sequence encoding a promoter functionally linked to a DNA sequence coding for a juvenile hormone esterase which is linked in frame to a gene coding for the heterologous protein under conditions wherein the heterologous protein is expressed and secreted from the cell.

14. The method of claim 13 wherein the promoter is selected from the group consisting of a viral promoter, an insect cellular promoter and a mammalian promoter.

15. The method of claim 13 wherein the expression cassette further comprises a DNA sequence encoding an enhancer functionally linked to the promoter.

16. The method of claim 13 wherein the juvenile hormone esterase gene is linked in frame to the gene encoding the heterologous protein by a linking sequence.

17. The method of claim 15, wherein the enhancer is a viral enhancer.

* * * * *

SEQUENCE LISTING

<160> NUMBER OF SEQ ID NOS: 11

<210> SEQ ID NO 1
<211> LENGTH: 43
<212> TYPE: DNA
<213> ORGANISM: Bombyx mori

<400> SEQUENCE: 1
aaaggatcca atgccacatc atcatcatca tcatggcggc ggc     43

<210> SEQ ID NO 2
<211> LENGTH: 42
<212> TYPE: DNA
<213> ORGANISM: Bombyx mori

<400> SEQUENCE: 2
aaaaccatgg cctgggtcct tgtcgtcgtc gtcgccgccg cc     42

<210> SEQ ID NO 3
<211> LENGTH: 28
<212> TYPE: DNA
<213> ORGANISM: Bombyx mori

<400> SEQUENCE: 3
gggctaccat ggagaaaaaa atcactgg                                    28

<210> SEQ ID NO 4
<211> LENGTH: 29
<212> TYPE: DNA
<213> ORGANISM: Bombyx mori

<400> SEQUENCE: 4
gggtgctcta gaatttctgc cattcatcc                                   29

<210> SEQ ID NO 5
<211> LENGTH: 30
<212> TYPE: DNA
<213> ORGANISM: Bombyx mori

<400> SEQUENCE: 5
aaaaggatcc atgacttcac acgtactcgc                                  30

<210> SEQ ID NO 6
<211> LENGTH: 29
<212> TYPE: DNA
<213> ORGANISM: Bombyx mori

<400> SEQUENCE: 6
aaaaggatcc ttcaagcggg cttctactg                                   29

<210> SEQ ID NO 7
<211> LENGTH: 42
<212> TYPE: DNA
<213> ORGANISM: Bombyx mori

<400> SEQUENCE: 7
aaaagcatgc cctgggtcct tgtcgtcgtc gtcgccgccg cc                    42

<210> SEQ ID NO 8
<211> LENGTH: 25
<212> TYPE: DNA
<213> ORGANISM: Bombyx mori

<400> SEQUENCE: 8
tgtgggcatg cagagcgtgg cgaag                                       25

<210> SEQ ID NO 9
<211> LENGTH: 31
<212> TYPE: DNA
<213> ORGANISM: Bombyx mori

<400> SEQUENCE: 9
cgacattcaa atctagaata agtccccta c                                 31

<210> SEQ ID NO 10
<211> LENGTH: 17
<212> TYPE: PRT
<213> ORGANISM: Unknown
<220> FEATURE:
<223> OTHER INFORMATION: Description of Unknown Organism:synthetic

<400> SEQUENCE: 10

Pro His His His His His His Gly Gly Gly Asp Asp Asp Asp Lys Asp
 1               5                  10                  15

Pro

```
<210> SEQ ID NO 11
<211> LENGTH: 1694
<212> TYPE: DNA
<213> ORGANISM: Heliothis virescens

<400> SEQUENCE: 11
atgacttcac acgtactcgc gctcgccttc cttctacacg cgtgcacagc gctggcgtgg      60
caggagacaa attcgcgcag cgtggtcgcc catctggact ccggcattat acgcggcgtg     120
ccgcgctcag cggatggcat caagttcgcc agcttcctag gagtgcccta cgctaagcag     180
cctgttggag aactcaggtt taaggagctc gagcctctag aaccttggga taatatcctg     240
aacgcaacaa atgaaggacc catctgcttc caaacagatg tattatacgg gaggctcatg     300
gcggcaagcg agatgagcga ggcttgcata tacgccaaca ttcatgttcc atggcaaagc     360
cttccccgag tgaggggac cacacctta cggcctatcc tggtgttcat acatggtgga      420
ggatttgctt tcggctccgg ccacgaggac ctacacggac cagaatattt ggtcactaag     480
aatgtcatcg tcatcacgtt taattacaga ttgaacgtct tcggtttcct gtccatgaac     540
acaacaaaaa tccccgggaa tgccggtctc cgggatcagg taaccctgtt gcgctgggtg     600
caaaggaacg ccaagaattt cggaggagac cccagcgaca tcaccatagc ggggcagagc     660
gctggtgcat cagctgcgca tctactgact cttctaaag ctactgaagg tcttttcaaa     720
agagcgattc tgatgagcgg aacaggaatg agctacttct ttactacttc tccacttttc     780
gcggcctaca tttcgaaaca gttgttgcaa atcctgggca atcaacgaga cggatccgaa     840
gaaatacatc ggcagctcat cgacctaccc gcagagaaac tgaacgaggc taacgccgtc     900
ctgattgaac aaattggcct gacaaccttc ctccctattg tggaatcccc actacctgga     960
gtaacaacca ttattgacga tgatccagaa atcttaatag ccgaaggacg cggcaagaat    1020
gttccacttt taataggatt taccagctca gaatgcgaga cttccgcaa tcgactattg      1080 aactttgatc tcgtcaaaaa gattcaggac aatcctacga tcataatacc gcctaaactg    1140
ttatttatga ctccaccaga gctgttgatg gaattagcaa agactatcga gagaaagtac    1200
tacaacggta caataagtat cgataacttc gtaaaatcat gttcagatgg cttctatgaa    1260
taccctgcat tgaaactggc gcaaaaacgt gccgaaactg gtggagctcc actgtacttg    1320
taccggttcg cgtacgaggg tcagaacagc atcatcaaga aggtaatggg gctgaaccac    1380
gagggtgtcg gccacattga ggacttaacc tatgtgttta aggtcaactc tatgtccgaa    1440
gctctgcacg catcgccttc tgagaatgat gtgaaaatga agaatctaat gacgggctat    1500
ttcttaaatt ttataaagtg cagtcaaccg acatgcgaag acaataactc attggaggtg    1560
tggccggcta acaacggcat gcaatacgag gacattgtgt ctcccaccat catcagatcc    1620
aaggagttcg cctccagaca acaagacatt atcgagttct tcgacagctt caccagtaga    1680
agcccgcttg aatg                                                      1694
```